US00PP37464P2

(12) United States Plant Patent
Smit

(10) Patent No.: US PP37,464 P2
(45) Date of Patent: Jun. 9, 2026

(54) ***PEPEROMIA* PLANT NAMED 'EC-PEPE-2501'**

(50) Latin Name: *Peperomia caperata*
Varietal Denomination: EC-PEPE-2501

(71) Applicant: Eden Collection B.V., Sappemeer (NL)

(72) Inventor: Obed Jacob Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 19/235,306

(22) Filed: Jun. 11, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

PUBLICATIONS

CPVO Application Consultation (Community Plant Variety Office); Version 4. 23.11; citation for 'EC-PEPE-2501'. Retrieved on Sep. 17, 2025.*

* cited by examiner

*Primary Examiner* — Susan Mccormick Ewoldt

(57) ABSTRACT

A new and distinct cultivar of *Peperomia* plant named 'EC-PEPE-2501' is disclosed, characterized by acute foliage with very dark green upper sides and red under sides. Plants are larger than most *Peperomia caperata*. The new cultivar is a *Peperomia*, typically used as an ornamental plant.

3 Drawing Sheets

Latin name of the genus and species: *Peperomia caperata.*

Cultivar denomination: 'EC-PEPE-2501'.

BACKGROUND OF THE INVENTION

The new cultivar is a product of a planned breeding program to produce distinct and better performing *Peperomia* cultivars. The new cultivar was selected as a seedling resulting from the crossing of *Peperomia caperata* '#2020.01' (female parent), and '#2020.07' (male parent), two unpatented cultivars from the inventor's breeding line. The crossing was made by the inventor, Obed J. Smit, a citizen of the Netherlands in 2021. 'EC-PEPE-2501' was selected by the inventor in 2023 at a commercial greenhouse in Sappemeer, the Netherlands.

Asexual reproduction of the new cultivar 'EC-PEPE-2501' by terminal cuttings was first performed in Sappemeer, the Netherlands at a commercial greenhouse in March 2023, and has shown that the unique features of this cultivar are stable and reproduced true to type through successive generations.

SUMMARY OF THE INVENTION

The cultivar 'EC-PEPE-2501' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2501'. These characteristics in combination distinguish 'EC-PEPE-2501' as a new and distinct *Peperomia* cultivar:

1. Acute foliage.
2. Very dark green upper leaf color with red under leaf color.
3. Larger plant habit than most other *Peperomia caperata* known to the inventor.

PARENT COMPARISONS

Plants of the new cultivar 'EC-PEPE-2501' are similar to plants of the female parent in most horticultural characteristics, however, plants of the new cultivar 'EC-PEPE-2501' differ from in the following characteristics:

1. Leaf upper side color of the new cultivar is very dark green, while the leaf upper side color of the seed parent is darker, almost black.
2. Leaf under side color of the new cultivar red, while the leaf under side color of the seed parent is very dark green, almost black.
3. Plants of the new cultivar are about 40% smaller than plants of the seed parent.

Plants of the new cultivar 'EC-PEPE-2501' are similar to plants of the male parent in most horticultural characteristics, however, plants of the new cultivar 'EC-PEPE-2501' differ in the following characteristics:

1. Leaf upper side color of the new cultivar is very dark green, while the leaf upper side color of the pollen parent is green.
2. Leaves of the new cultivar are approximately 30% larger than leaves of the pollen parent.
3. Plants of the new cultivar are about 20% larger than plants of the pollen parent.

COMMERCIAL COMPARISONS

Plants of the new cultivar 'EC-PEPE-2501' are similar to plants of the commercial cultivar *Peperomia caperata* 'EC- PEPE-2101', U.S. Plant Pat. No. 34,603. However, plants of the new cultivar differ in the following characteristics:

1. Leaf upper side color of the new cultivar is very dark green, while the leaf upper side color of this comparator is grey with dark green veins.
2. Leaf under side color of the new cultivar is red, while leaf under side color of this comparator is light green with red veins.
3. Leaves of the new cultivar are round at the base with a pointed leaf end, while leaves of this comparator are round.
4. Leaves of the new cultivar are much larger than leaves of this comparator.
5. Plants of the new cultivar are larger than plants of this comparator.

Plants of the new cultivar 'EC-PEPE-2501' are similar to plants of the commercial cultivar *Peperomia caperata* 'Schumi Red', unpatented. However, plants of the new cultivar differ in the following characteristics:

1. Leaf color of the new cultivar is very dark green on the upper side, red on the under side. Leaf color of this comparator is fully red on upper and under sides.
2. Leaves of the new cultivar are much larger than leaves of this comparator.
3. Plants of the new cultivar are larger than plants of this comparator.

BRIEF DESCRIPTION OF THE PHOTOGRAPHS

The accompanying photograph in FIG. 1 illustrates in full color a typical blooming plant of 'EC-PEPE-2501' grown in a greenhouse. The plant is approximately 30 weeks of age.

Figure 1:
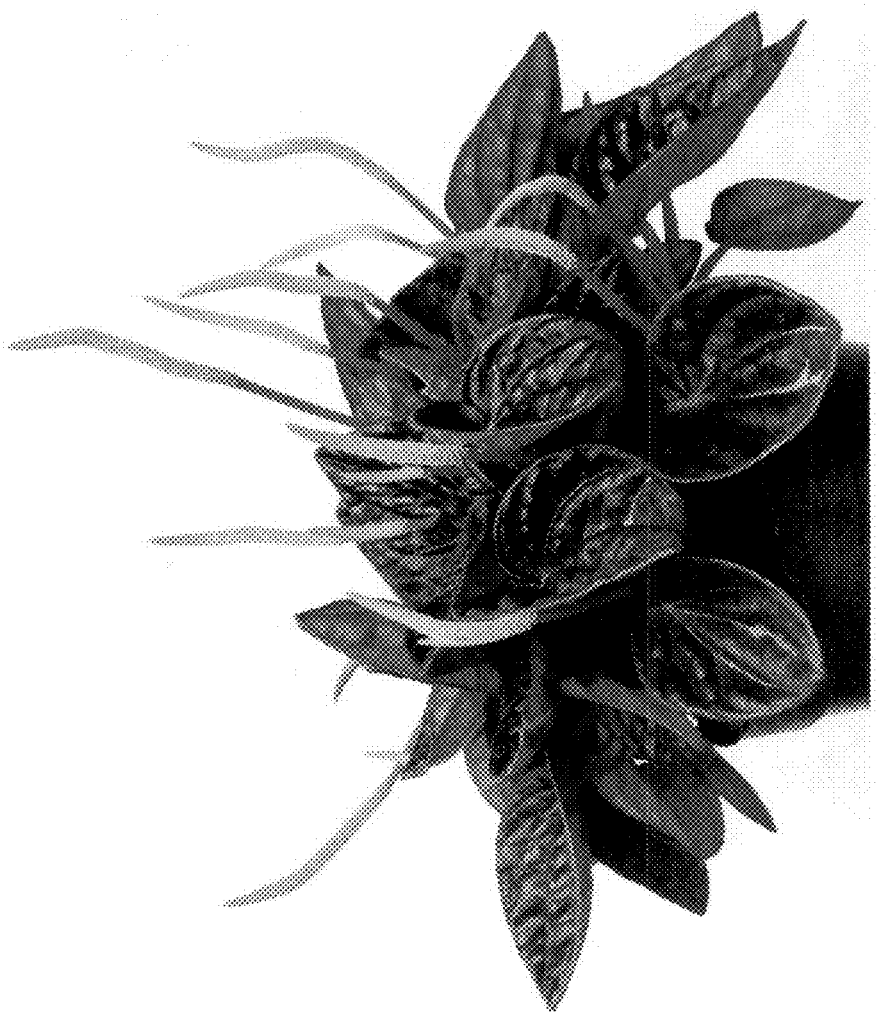
Figure 2:
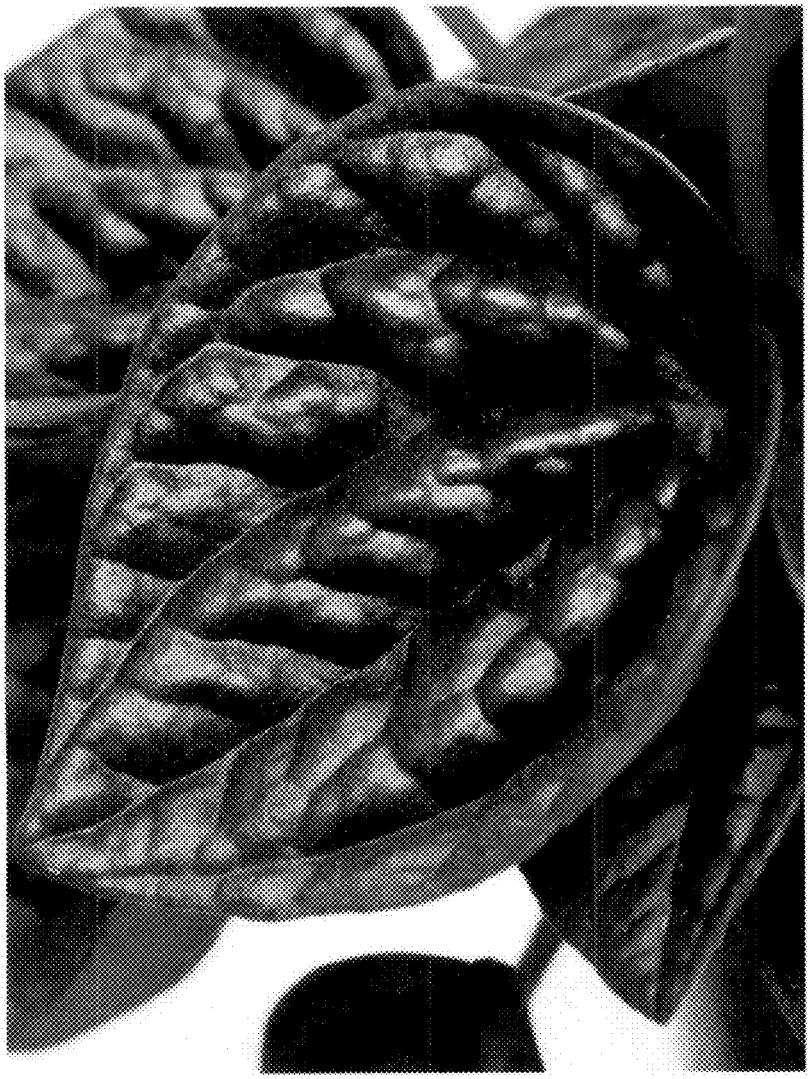
FIG. 2 illustrates a close-up of the foliage.
Figure 3:
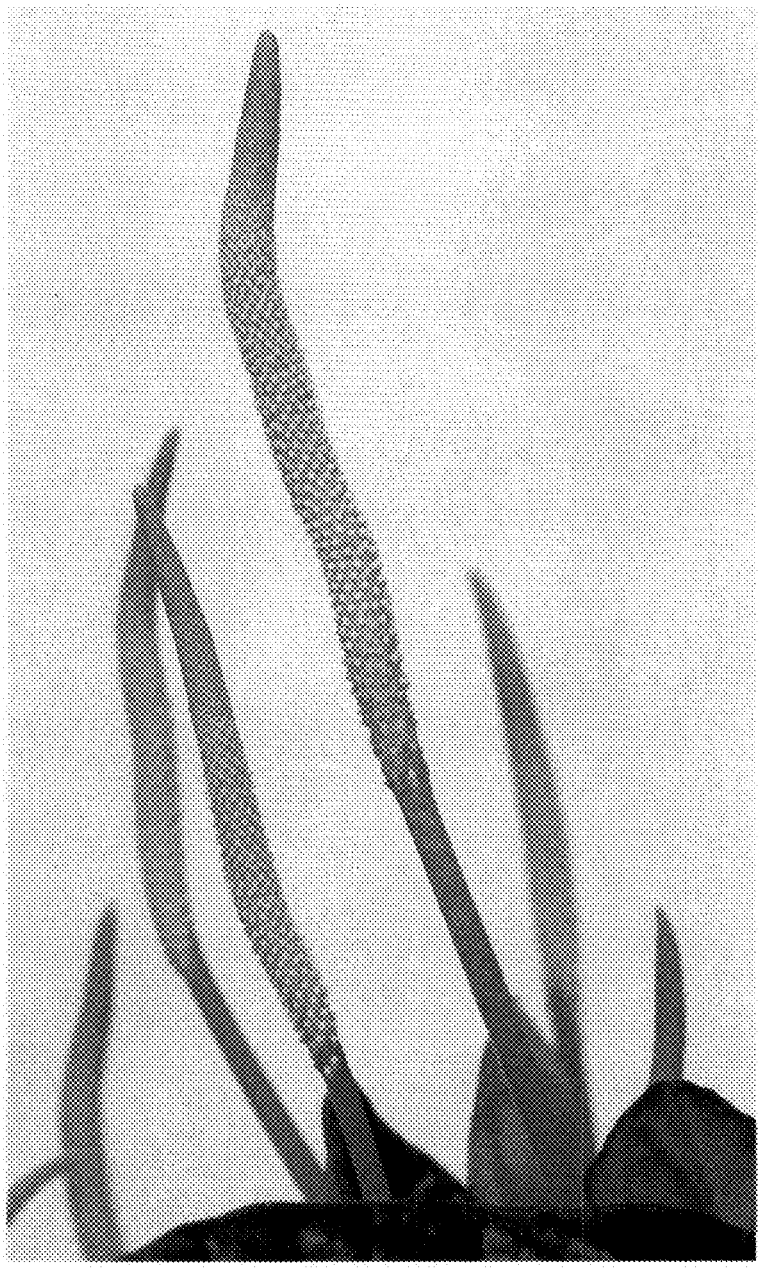
FIG. 3 is a close-up view of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2501' plants at 30 weeks of age, grown in a greenhouse in April in Sappemeer, the Netherlands. The growing temperature ranged from 17° C. to 18° C. at night to 19° C. to 21° C. during the day. Measurements and numerical values represent averages of typical flowering types.

Botanical classification: *Peperomia caperata* 'EC-PEPE-2501'.

PROPAGATION

Time to initiate roots: About 21 days at 21° C. in summer; 28 days at 21° C. in winter.

Time to produce rooted cutting: About 100 days at 21° C. in summer; 120 days at 21° C. in winter.

Description of roots: Herbaceous, fine, moderately dense, freely branching. White in color, not accurately measured with R.H.S. chart.

PLANT

Plant type: Perennial potted plant.

Plant shape: Flattened to flattened globular with inflorescences carried in slightly above and above the foliar plane.

Plant spread: Approximately 33.9 cm.

Height: 15.9 cm to top of foliar plane; 24.3 cm to top of floral plane.

Growth rate: Moderate.

Plant vigor: Moderate.

Age of plant described: Approximately 10 months.

Branching habit: Leaves in rosettes, eventually forming very short, thick stems/branches.

Pinching: Pinching not required.

Number of primary (main) branches per plant: Average 7.

Main branches:

*Length*.—Average: 2.2 cm.

*Diameter*.—Average: 0.8 cm.

Internode length: Average: Less than 0.6 cm.

Appearance and shape: Succulent, thick and rounded.

Luster: Matte.

Aspect/angle from vertical: Average angle: 15°.

Strength: Moderately strong.

Color:

*Developing*.—RHS Greyed-Purple 187A.

*Mature*.—RHS Greyed-Purple N186C.

*At internodes*.—RHS Greyed-Purple N186C.

Pubescence: None.

Plant fragrance: None.

FOLIAGE

Leaf:

*Arrangement*.—Alternate, single.

*Quantity*.—Average 11.

*Average length*.—8.4 cm.

*Average width*.—6.7 cm.

*Shape of blade*.—Cordate.

*Whole leaf aspect*.—Concave to strongly concave with revolute margin.

*Apex*.—Broad, bluntly acute.

*Base*.—Cordate, lobes touching to slightly overlapping.

*Margin*.—Entire, slightly revolute.

*Texture of top surface*.—Glabrous, smooth, moderately leathery, strongly bullate.

*Texture of bottom surface*.—Glabrous, smooth, moderately leathery.

*Pubescence*.—None.

*Luster, upper side*.—Glossy.

*Luster, under side*.—Very slightly glossy, velvety.

*Rugosity*.—Both sides non-rugose.

*Color*.—Young foliage upper side: RHS Black 203D, slightly flushed Greyed-Green N189A. Young foliage under side: RHS Greyed-Purple 183D. Mature foliage upper side: A blend of RHS Green 139A and Black 203D; area adjacent to main veins tinged slightly less green. Mature foliage under side: RHS Greyed-Purple 185A, with a silvery haze.

*Venation*.—Pattern: Parallel, strongly furrowed. Venation color upper side: RHS Black 203D, very slightly flushed Green 139A. Venation color under side: RHS Greyed-Purple 187A.

*Petiole*.—Average Length: 7.7 cm. Diameter: Upper side of petiole flattened, average diameter at widest (horizontal): 0.5 cm, average diameter at narrowest (vertical): 0.3 cm. Texture: Glabrous, smooth. Luster: Both sides slightly glossy. Strength: Low. Color, upper side: RHS Greyed-Purple 183A. Color, under side: RHS Greyed-Purple 183B.

FLOWER

Inflorescence:

*Arrangement*.—Axillary spike.
*Inflorescence type and form*.—Spike.
*Inflorescence height*.—Average: 7.1 cm (excluding peduncle).
*Inflorescence diameter*.—Average: 0.6 cm.
*Quantity of flowers per inflorescence*.—Average 900 individual flowers per spike.
*Quantity of flowers per plant*.—Average 9,600.
*Quantity of flower buds per plant*.—Average 4,800.
*Quantity of flowers and buds per plant*.—Average 14,400.
*Natural flowering season*.—Spring.

Flower bud:

*Flower bud length*.—0.2 mm.
*Flower bud diameter*.—0.2 mm.
*Flower bud shape*.—Flattened, circular.
*Flower bud texture*.—Glabrous, smooth, slightly velvety.
*Flower bud luster*.—Slightly glossy.
*Flower bud color*.—Near RHS Green 138B.

Flower:

*Flower type and form*.—Individual flowers are very small and consist of 1 bract, 2 stamens and a single pistil.
*Flower aspect*.—Outward.
*Flowering habit*.—Very freely.
*Fragrance*.—None.
*Flower shape*.—Rotate, consisting of 1 bract, 2 stamens and 1 pistil only; no petals and sepals present.
*Flower height*.—Average: 1 mm.
*Flower diameter*.—Average: 0.7 mm.
*Flower length*.—Average: 0.7 mm.
*Flower longevity on plant*.—Average one month.
*Persistence*.—Self-cleaning.

Peduncles:

*Terminal peduncle length*.—Average 12.5 cm.
*Terminal peduncle diameter*.—Average 4 mm.
*Peduncle angle to lateral branch axis*.—Average angle 30°.
*Peduncle strength*.—Weak.
*Peduncle texture*.—Glabrous, smooth.
*Peduncle luster*.—Moderately glossy.
*Peduncle color*.—RHS Greyed-Purple 185A, slightly lighter at the base.

Floral bracts:

*Quantity per flower*.—One below each individual flower.
*Shape*.—Orbicular.
*Length*.—0.5 mm.
*Width*.—0.5 mm.
*Color*.—Near RHS Yellow-Green 158C; edged near White NN155D; edges slightly transparent.

REPRODUCTIVE ORGANS

Stamens:

*Number*.—Average 2.
*Filament length*.—Average 0.3 mm.
*Filament color*.—Near RHS Green 138B.

Anther:

*Shape*.—Ovate.
*Length*.—Average 0.4 mm.
*Width*.—Average 0.15 mm.
*Color*.—RHS Greyed-Yellow 160C.
*Pollen*.—Low.
*Pollen color*.—RHS Greyed-Yellow 160C.
*Pistil*.—Number: Average 1. Length: Average 0.5 mm.
*Stigma*.—Shape: Flattened, hairy, circular. Length: Average 0.7 mm. Diameter: Average 0.5 mm. Color: RHS Yellow-Green 144D. Style: Sessile. Ovary color: RHS Yellow-Green 145B.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures up to 40° C. Hardy to USDA zones 10 to 12. Moderate tolerance to rain.

What is claimed is:

1. A new and distinct cultivar of *Peperomia* plant named 'EC-PEPE-2501' as herein illustrated and described.

* * * * *